(12) United States Patent
Hacker

(10) Patent No.: US 6,988,075 B1
(45) Date of Patent: Jan. 17, 2006

(54) PATIENT-CONTROLLED MEDICAL INFORMATION SYSTEM AND METHOD

(76) Inventor: L. Leonard Hacker, 319 9th St., SE., Washington, DC (US) 20003-2116

(*) Notice: Subject to any disclaimer, the term of this patent is extended or adjusted under 35 U.S.C. 154(b) by 456 days.

(21) Appl. No.: 09/525,244

(22) Filed: Mar. 15, 2000

(51) Int. Cl.
*G06F 17/60* (2006.01)

(52) U.S. Cl. .............................................. 705/3; 705/2

(58) Field of Classification Search ................ 705/2–3; 701/32; 128/903, 920; 177/25.19

See application file for complete search history.

(56) References Cited

U.S. PATENT DOCUMENTS

| | | | | |
|---|---|---|---|---|
| 5,664,109 A | * | 9/1997 | Johnson et al. .................. | 705/2 |
| 5,737,539 A | * | 4/1998 | Edelson et al. .................. | 705/2 |
| 5,772,585 A | * | 6/1998 | Lavin et al. ................ | 128/920 |
| 5,823,948 A | * | 10/1998 | Ross et al. .................. | 600/300 |
| 5,924,074 A | * | 7/1999 | Evans ............................ | 705/2 |
| 6,024,699 A | * | 2/2000 | Surwit et al. ............... | 128/903 |
| 6,032,119 A | * | 2/2000 | Brown et al. ............ | 177/25.19 |
| 6,076,166 A | * | 6/2000 | Moshfeghi et al. ............ | 705/3 |
| 6,330,499 B1 | * | 12/2001 | Chou et al. ................... | 701/32 |

FOREIGN PATENT DOCUMENTS

WO   WO2004102393 A1 * 11/2004

OTHER PUBLICATIONS

Business Wire, Partners with MedTouch Internet Health Service, Health Profiling software helps individuals manage personal health risks, Jun. 22, 1998, Business Editors/Heatlh & Medical Writers, p. 1.*

* cited by examiner

*Primary Examiner*—Joseph Thomas
*Assistant Examiner*—Robert Morgan
(74) *Attorney, Agent, or Firm*—Roberts, Abokhair & Mardula, LLC

(57) ABSTRACT

An electronic medical record system and service is disclosed for centrally storing patients medical records electronically on a database for patient-controlled remote access by both patients and medical providers. The system stores a plurality of patient medical records on a medical information database via a medical information server connected to a network. A plurality of medical provider computers connected to the network have software to communicate with the medical information server. Patients supply authorization means to allow medical provider computers to access patient-selected portions of the patient's medical record for viewing and updating of the patient's medical record. Additionally, patients can access all portions of their medical record using browser software on any browser-enabled device connected to the network.

46 Claims, 5 Drawing Sheets

PATIENT-CONTROLLED MEDICAL INFORMATION SYSTEM AND METHOD

The present invention is drawn to an electronic medical record system and service. In particular, it is drawn to a system and service for centrally storing patients medical records electronically on a database for patient-controlled remote access by both patients and medical providers.

BACKGROUND

While the technology has been developed to provide the capability of storing medical records electronically, the use and implementation of electronic medical records has not developed significantly beyond the traditional physician-controlled medical record system based on paper medical records.

U.S. Pat. No. 6,018,713 to Coli et al. discloses a network-based system and method for ordering and reporting the cumulative results of medical tests. The system includes a computer operated at a physician location (such as a hospital or physician office) to order tests, retrieve and store statistical data or status the progress of previously ordered tests, and at least one lab site computer for receiving physician requests for tests and reporting their results. The physician computer and lab site computer are interconnected by a computer network. The physician computer receives a physician or user request for ordering a test, causes a test request message to be sent to the lab site computer, causes a request for statistical data to be sent to the network, and receives statistical data from the network. The lab site computer is programmed to receive a test request message and to cause a test results message or a test status message to be sent to the physician computer. The system also includes a patient database computer which generates longitudinal medical reports, and performs test ordering functions, real time results reporting, and intelligent physician alerting and decision support functions, as appropriate in response to requests from other computers in the system. No patient access to or control of their medical records is disclosed.

U.S. Pat. No. 5,974,389 to Clark et al discloses a patient medical record system that includes a number of caregiver computers, and a patient record database with patient data coupled to the caregiver computers for selectively providing access to the patient data from one of the caregiver computers responsive to a predetermined set of access rules. The predetermined set of rules includes a rule that access to a predetermined portion of the patient data by a first caregiver must be terminated before access to the same predetermined portion by a second caregiver is allowed. No patient access to or control of their medical records is disclosed.

U.S. Pat. No. 5,924,074 to Evans discloses a medical records system that creates and maintains all patient data electronically. The system captures patient data, such as patient complaints, lab orders, medications, diagnoses, and procedures, at its source at the time of entry using a graphical user interface having touch screens. Using pen-based portable computers with wireless connections to a computer network, authorized healthcare providers can access, analyze, update and electronically annotate patient data even while other providers are using the same patient record. The system likewise permits instant, sophisticated analysis of patient data to identify relationships among the data considered. Moreover, the system includes the capability to access reference databases for consultation regarding allergies, medication interactions and practice guidelines. The system also includes the capability to incorporate legacy data, such as paper files and mainframe data, for a patient. No patient access to or control of their medical records is disclosed.

U.S. Pat. No. 5,772,585 to Lavin et al. discloses a system and method for managing patient medical information to facilitate data management and improve physician access to and recordal of examination data is described. The method comprises a computer aided process including the steps of scheduling appointments, entering and displaying data to a physician, updating the patient data with progress notes concurrently with an examination, displaying allergy warnings and recording a diagnosis based on the progress notes. A common graphic user interface is also disclosed to facilitate operation of the preferred system and method. The system and method are implemented with a relational database operating on data tables which store information input into the user interface. No patient access to or control of their medical records is disclosed.

U.S. Pat. No. 5,845,253 to Rensimer et al. discloses system and method for processing patient data permits physicians and other medical staff personnel to record, accurately and precisely, historical patient care information. An objective measure of a physician's rendered level of care, as described by a clinical status code, is automatically generated. Data elements used in the determination of the generated clinical status code include a level of history of the patient, a level of examination of the patient, a decision-making process of the physician treating the patient, and a "time influence factor." The quantity and quality of care information for a particular patient is enhanced allowing future care decisions for that patient to be based on a more complete medical history. Enhanced care information can be used in outcome studies to track the efficacy of specific treatment protocols. Archiving of patient information is done in a manner which allows reconstruction of the qualitative aspects of provided medical services. The medical care data can be recorded, saved, and transferred from a portable system to a larger stationary information or database system. No patient access to or control of their medical records is disclosed.

U.S. Pat. No. 5,867,821 to Ballantyne et al. discloses a method and apparatus used for the distribution and administration of medical services, entertainment services, electronic medical records, educational information, etc. to a patient's individual electronic patient care station (PCS) interconnected to a master library (ML) which stores data in digital compressed format, through a local medical information network. The patient/medical personnel interact with this medical information network through the unique PCS and receives the requested service or data from the master library. The data is then displayed either on the associated television set or video monitor or through wireless/IR communications to a peripheral personal data assistant (pen based computer technology) The data for text, audio, and video information is all compressed digitally to facilitate distribution and only decompressed at the final stage before viewing/interaction. Column 9 discloses patient access to "clinical data that the patient has been allowed access", but not access to their entire medical record. No patient control of medical records is disclosed.

U.S. Pat. No. 5,890,129 to Spurgeon discloses an information-exchange system for controlling the exchange of business and clinical information between an insurer and multiple health care providers. The system includes an information-exchange computer that is connected over a local area network to an insurer computer using a proprietary database and over the Internet to health-care provider computers using open database-compliant databases. The information-exchange computer receives subscriber insurance data from the insurance computer database, translates the insurance data into an exchange database, and pushes the subscriber insurance data out over the Internet to the computer operated by the health-care provider assigned to each subscriber. The information-exchange system stores the data in the provider database. The information-exchange system also provides for the preparation, submission, processing, and payment of claims over the local area network and with push technology over the Internet. In addition, prior authorization requests may be initiated in the provider computers and exchanged over the information-exchange system for review by the insurer computer. Processed reviews are transmitted back to the provider computer and to a specialist computer, if required, using push technology over the Internet. No patient access to or control of their medical records is disclosed.

U.S. Pat. No. 5,664,109 to Johnson et al. discloses a central medical record repository for a managed health care organization that accepts and stores medical record documents in any format from medical service providers. The repository then identifies the document using information automatically extracted from the document and stores the extracted data in a document database. The repository links the document to a patient by extracting from the document demographic data identifying the patient and matching it to data stored in a patient database. Data is extracted automatically from medical records containing "unstructured" or free-form text by identifying conventional organization components in the text and is organized by executing rules that extract data with the aid of such information. Documents for a patient are retrieved by identifying the patient using demographic data. No patient access to or control of their medical records is disclosed.

U.S. Pat. No. 5,325,294 to Keene discloses a system for confidentially reporting medical test results to partners of patients. No patient access to or control of their medical records is disclosed.

U.S. Pat. No. 5,671,282 to Wolf et al. discloses a document verification and tracking system useful for prescription authorization (see FIGS. 3–4). No patient access to or control of their medical records is disclosed.

U.S. Pat. No. 5,546,580 to Seliger et al. discloses a method for coordinating updates to medical database in a medical information system that permits concurrent charting from different workstations and medical instruments. A first data value for a record is entered at a first workstation and a second data value for the record is entered at a second workstation without locking either workstation during data entry. The new data values are stored in the medical database after completion of data entry at each workstation, and a correction history is recorded. The correction history contains information as to the update of the record with the first data value and the second data value. The record is updated with the first and second data values without aborting user activities or notifying a user that an update conflict has occurred. After the new data values are stored in the medical database, all workstations containing a copy of the record are updated to reflect the current state of the record. No patient access to or control of their medical records is disclosed.

U.S. Pat. No. 5,960,085 to de la Huerga discloses a system utilizing a personal identification badge to collect data and to provide access to a computer terminal. The personal identification badge includes circuitry and transceiver components for transmitting identification information and exchanging other digital information with a computer terminal and other compatible devices. The personal identification badge establishes a wireless communication link with a computer terminal to allow a user to logon to the terminal. When a user leaves the computer terminal, the communication link is terminated, causing the computer terminal to lock the keyboard, blank the monitor, and/or logoff the user if the communication link is not restored within a sufficient time period. The personal identification badge includes means for encrypting and signing digital information. Adapted for use within a hospital, the system provides further means for establishing an affiliation between a personal identification badge and a patient, for collecting digital information from electronic devices that record or gather data regarding the status of a patient, for digitizing and recording dictation spoken into the personal identification badge, and for modifying the digital information so collected to conform to standards, such as those of a Java applet or the hypertext markup language, for interactive display on a universal display browser. No patient access to or control of their medical records is disclosed.

U.S. Pat. No. 5,778,225 to Supernaw-Issen et al. discloses an object oriented patient record 464. No patient access to or control of their medical records is disclosed.

U.S. Pat. No. 5,930,804 to Yu et al. discloses biometric authorization as a substitute for passwords for medical transactions such as emergency access to medical records (see column 2, lines 40–48). No patient access to or control of their medical records is disclosed.

U.S. Pat. No. 5,737,539 to Edelson et al. discloses an electronic prescription creation system for use by professional prescribers at the point of care has a prescription division subsystem permitting creation of a single prescription to be automatically divided into two components for fulfilment of one portion quickly and locally at higher cost and of another portion by remote mail order taking more time but providing a cost saving for a major part of the prescription. The prescription creation system has an ability to access remote source databases for system presentation to the prescriber of relevant, authorized and current drug, drug formulary and patient history information, with dynamic creation of a transient virtual patient record, the information being presented to the prescriber before completion of the prescription, permitting enhancement of the quality of prescribing decisions. No patient access to or control of their medical records is disclosed.

U.S. Pat. No. 6,000,828 to Leet discloses a computer implemented method and system for improving drug treatment of patients in local communities by providing drug treatment protocols for particular disease states, such as Diagnosis Related Group (DRG) classifications. The protocol contains ranked recommendations for drug treatments of the disease state, and the computer system collects information about the risks and benefits of the drug treatments. The information collected about the treatments is used to modify the rankings of the drug treatments in the protocol. In one specific embodiment of the system, where the disease state has a microbial etiology and the treatments are antimicrobial drugs, the emergence of drug resistance is quickly detected by determining the percentage of microbial isolates that are found to be resistant to antimicrobial therapy in the community where the therapy is being provided (such as a community hospital or city-wide health care system). An increase in the percentage of resistant isolates produces a re-ranking of recommended drug therapies to avoid further use of the drug to which resistance has developed, and helps quickly introduce more effective drugs that will improve the effectiveness and lower the cost of treatment. In yet other embodiments, a sum of medication (e.g. dosing) errors and adverse effects (e.g. allergic reactions) are tracked by the system to identify drugs that are poorly tolerated in particular populations served by the hospital where the treatment is being provided. Data is collected about the safety and effectiveness of all types of drug therapies in the community being served, and this data is used to modify the drug protocols. No patient access to or control of their medical records is disclosed.

U.S. Pat. No. 5,823,948 to Ross, Jr. et al. discloses a system that provides: automatic incorporation of dictated text; medical records summary generation in medical English text; parsing dictation to data; prephrased text; automatic generation of medical record as consequence of data entry; automatic notation of allergies, significant medical conditions and pregnancy; pregnancy linking, automatically; security card—close on pull; multi-look grease board; outstanding orders listing for all patients in the department; department layout; room selection excludes occupied rooms; nurses notes to text; nurses notes from physician orders to nurses; lab request screen shows all previously ordered labs; therapeutics; ACLS recording; lacerations; doctor specific prescriptions and medication orders; review of systems; coding level alerts; differential diagnosis—filter to sex and age; diagnosis—fractures to text; doctor interval reexamination; patient instructions predicated on what was done; patient instruction video on demand; patient informed consent video on demand; video teleconferencing; electronic signatures; automatic backup and incremental backup with system on-line; critical management reports; and automatic research data extraction. No patient access to or control of their medical records is disclosed.

U.S. Pat. No. 4,916,441 to Gombrich discloses a handheld terminal with a scanner that is useful in a hospital environment for medical record keeping. No patient access to or control of their medical records is disclosed.

U.S. Pat. No. 4,857,716 to Gombrich et al. discloses a patient identification system for relating items with patients and ensuring that an identified item corresponds to an identified patient. The patient identification system includes a computer system interconnected to a plurality of remote terminals by conventional telephone wiring. The patient identification system further including a portable bar code reading device including a bar code wand, an LCD display and a key pad. The portable bar code reading device communicates via RF transmission with an RF/PLC modem. The bar code reading device is utilized to read a patient's unique bar codes on a patient's identification bracelet, bar codes on labels attached to various items in the hospital relating the item to a specific patient and bar codes on item labels whereby such items can be automatically correlated to a specific patient and checks performed at the computer system to ensure that the item properly corresponds to the identified patient. No patient access to or control of their medical records is disclosed.

The primary difference between prior art medical information systems and the present invention is the ability of the patient to access and control their medical data. Additionally, by implementing the system on the Internet, remote access is provided anywhere with Internet access and no specialized software other than a browser client is required by patients and medical providers. Medical providers can include pharmacies, medical laboratories, doctors, hospitals, and nurses.

As the Information Age has allowed more and more personal data to be collected, stored, used, and often even sold, privacy concerns of patients have assumed more importance. Many of the prior art electronic medical record systems have included mechanisms to provide some amount of privacy for patients by limiting access to medical records to authorized medical personnel, but have not allowed patients to decide which medical personnel will be authorized.

BRIEF SUMMARY OF THE INVENTION

The present invention is a system and service for centrally storing patients medical records electronically on a database for patient-controlled remote access by both patients and medical providers over a public network.

It is an object of the invention to provide patients greater access to and control over their medical records.

It is a further object of the invention to provide remote access to electronic medical records by patients or patient-authorized medical providers via a network, such as the Internet, using ordinary browser software.

It is another object of the invention to provide patient control over access to their records by using a patient supplied identifier, such as an ID/passphrase combination, bar code, smart card, or biometric sample, in order to access the electronic medical record.

It is another object of the invention to provide a system which can reduce medication and dosage mistakes.

It is another object of the invention to provide a system which can reduce dangerous medication interactions.

It is another object of the invention to provide a system which can assist in providing medical inventory control.

It is another object of the invention to provide a system which can automatically generate medical insurance claims.

It is another object of the invention to provide a system for scheduling and sending reminders for medical appointments and keeping track of the results.

It is another object of the invention to provide a system for verification to third parties of patients keeping appointments.

It is another object of the invention to provide a system to track patient medical costs.

It is another object of the invention to provide a system for allowing patients to approve access to their medical records for medical research, such as pharmacological studies.

It is another object of the invention to provide emergency access to patients' electronic medical records and notification of such access to patients.

It is another object of the invention to provide timely reporting of diagnostic test results to physicians and to patients.

It is another object of the invention to provide for transfer of electronic and hard copy medical records from other sources to the electronic patient medical record of the present invention.

It is another object of the invention to provide for an audit of patient medical records from other systems and means for correcting them when necessary.

It is yet another object of the invention to provide a system for linking the present invention with third parties such as navigational- or concierge-type services to improve urgent care services.

DETAILED DESCRIPTION OF THE INVENTION

Figure 1:
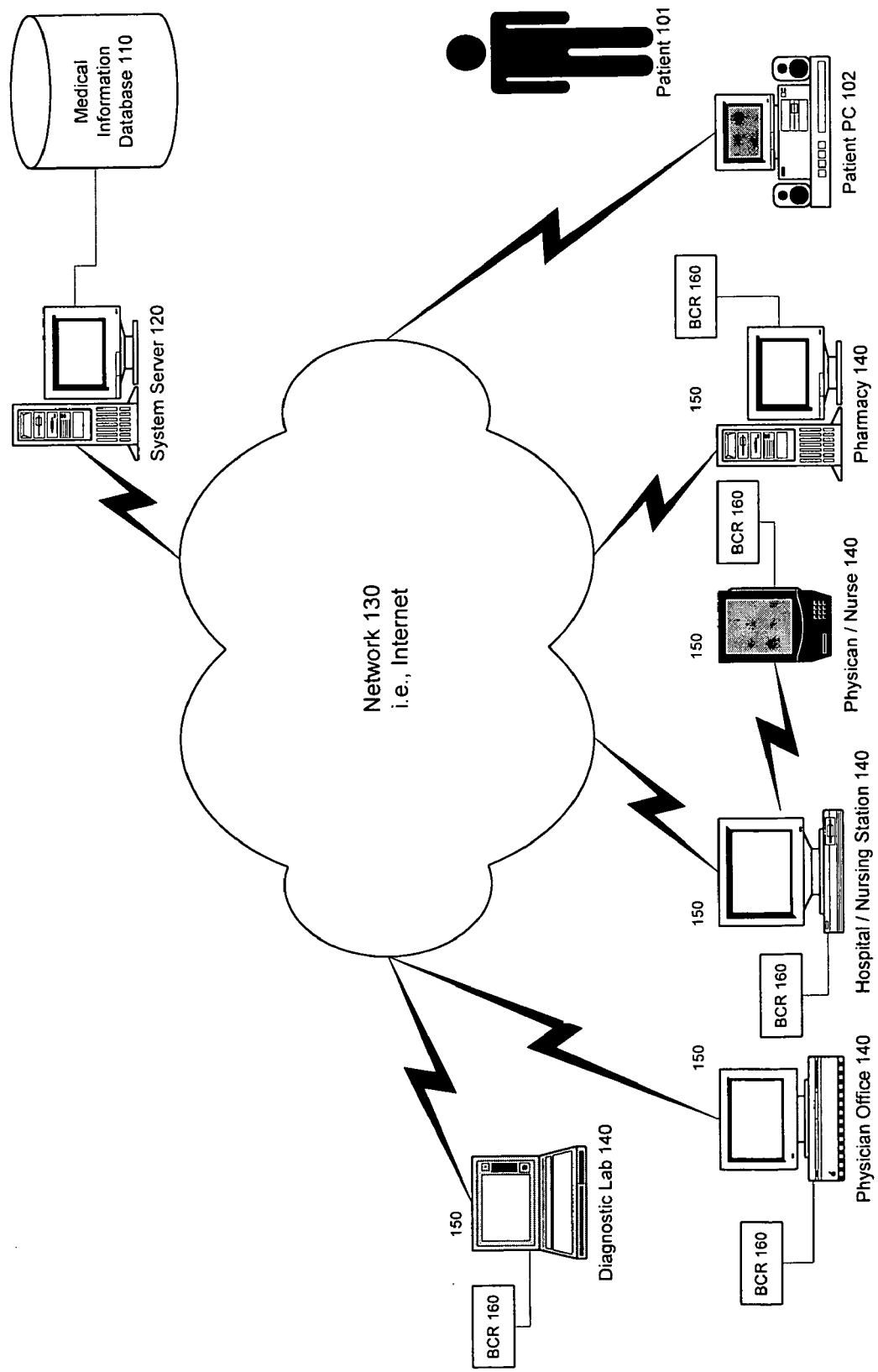
FIG. 1 discloses an overview of the elements involved with the present invention.

The medical information system and service of the present invention electronically stores patient medical records on a database and allows for remote access to the records by medical providers and patients. Patients control access to their record by providing a unique access identification means to a system server connected to the database.

As used herein, the term "medical" as used with both records and providers refers to generally accepted health-related areas served by physicians (M.D.s), surgeons, dentists, diagnostic clinicians, physical therapists, medical nurses, pharmacists, chiropractors, acupuncturists, and homeopaths.

As used herein, "browser" and "browser client" refer to generally available software programs which allows a person to read hypertext, such as, but not limited to, Netscape Navigator, MS Internet Explorer, NCSA Mosaic, Lynx, iCab, and W3 for personal computers, WAP-enabled software on wireless phones and other mobile computing devices, such as but not limited to automotive/navigational systems, or AvantGo, HandWeb, ProxiWeb, and Palmscape for handheld devices.

Although the system can use any suitable means for providing a unique access identification means for each patient, including assigned alpha-numeric passphrases, smart cards, and biometric samples (voiceprint, fingerprint, retina scan, DNA-ink, etc.), a preferred embodiment that will be used for this description is a card (or bracelet for hospitalized patients) with a unique bar code for each patient.

In practice, patients 101 register with a service of the present invention to have their medical records stored electronically by any suitable means on a medical information database 110. The database 110 is connected to a system server 120 that is connected to a publicly accessible network 130, which for this description is the Internet. Medical providers 140 have computers (PCs), handheld devices/personal digital assistants (PDAs), or other browser-enabled appliances or devices 150 for uploading and downloading/viewing medical data. Appropriate means for input of the unique access identification means, such as bar code readers (BCRs) 160 for bar coded cards and bracelets, can be used for patient identification and access. Particularly sensitive patient information can be passphrase protected so that the medical provider must get permission from the patient to gain access to it. The patient can also specify an emergency override of passphrase protection, and notification to the patient can be provided as to what information was released to emergency medical personnel, including time, location, pages accessed, etc.

When patients have allowed access, medical providers 140 can view appropriate portions of the patients medical record, and add information to the patient's medical record where appropriate. By limiting access to needed information, the patient's privacy can be increased. For example, pharmacists 140 would have access to prescription information but typically would not be given access to information concerning allergies, heart or liver conditions, age, weight, etc. since the checking/screening of this interaction information can be provided by software on the server 120. When a medical provider 140 feels they need access to blocked portions, the medical provider 140 can ask the patient for a patient-selected passphrase, and the patient can decide whether or not to grant access.

The system could also be set up to translate to and from foreign languages and to allow physicians 140 to electronically order diagnostic tests for patents with diagnostic labs 140.

Additionally, as shown in FIG. 1, PDAs 150 can be "connected" to the network through standard syncing with a computer 150 which is connected t the network.

In certain cases, medical providers 140 in very specific fields, such as dentistry, will have their own electronic medical record system and will need access to very little "outside" medical information. In these cases, appropriate or relevant "outside" medical information concerning the patient can be e-mailed to the medical provider by the server prior to a patient's appointment. This information can include allergies, medications, and relevant conditions such as pregnancy and heart/liver/kidney conditions.

The e-mail can be preauthorized and sent as part of a scheduling/reminder system on the server, can be sent upon a patient request, or can be sent under an autoresponder system based on patient ID when requested by a medical provider who has been given the appropriate information by the patient.

Updated information from the patient visit to the medical provider can be attached to a reply e-mail and, if necessary, translated by software on the server or otherwise sent to the server, by mail, fax, html form, etc., to update the patient medical record on the medical information database.

Figure 2:
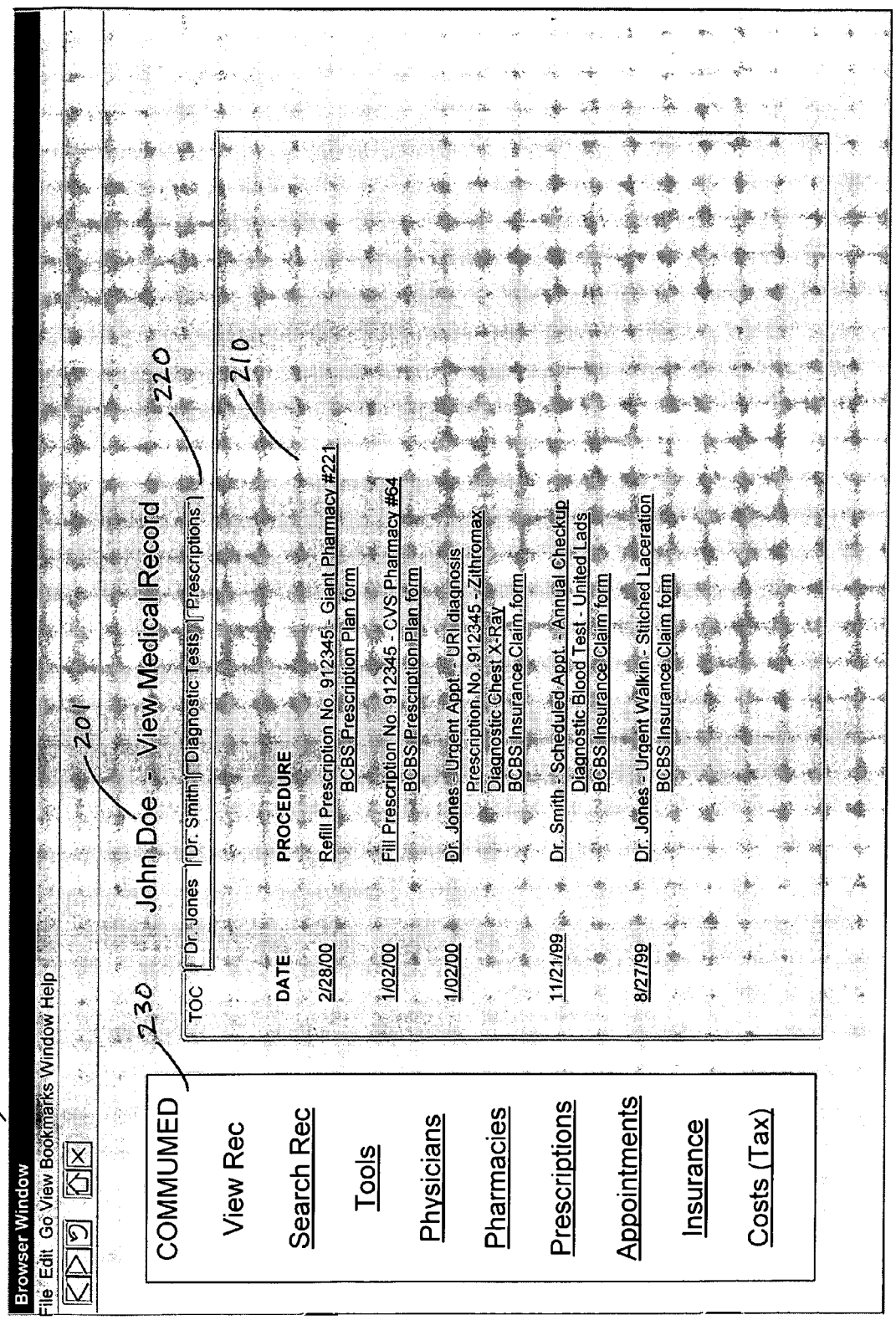
FIG. 2 discloses an example of a display screen for patient access to their medical record in accordance with the present invention.

Patients can access their medical data via a standard Web browser (preferably with strong encryption) and can use server-based software tools (using Java applets, for example) to graphically and textually access their records. Although access is shown through a patient PC 102, any other network-enabled browsing device can be used, including but not limited to hand-held computers (PDAs), WAP-enabled wireless phones, automobile-mounted computers, TV set-top browser systems, and Internet-specific browsing devices. Access can be controlled by a server-set cookie or patient-supplied alphanumeric identifier in combination with a patient-supplied passphrase. FIG. 2 discloses an example of a display screen from a browser 200 for patient access to their medical record. In this example, a patient 201 can access records from various medical events or procedures by selecting hypertext links 210 to view portions of their record. In the disclosed embodiment, hypertext links to the records can be chosen from a chronological table of contents (TOC), or from other categorized sections 220 such as by doctor, by diagnostic test, by prescription, etc. The browser window can also provide a menu 230 for selecting other tools for viewing data from the patient's record.

Figure 3:
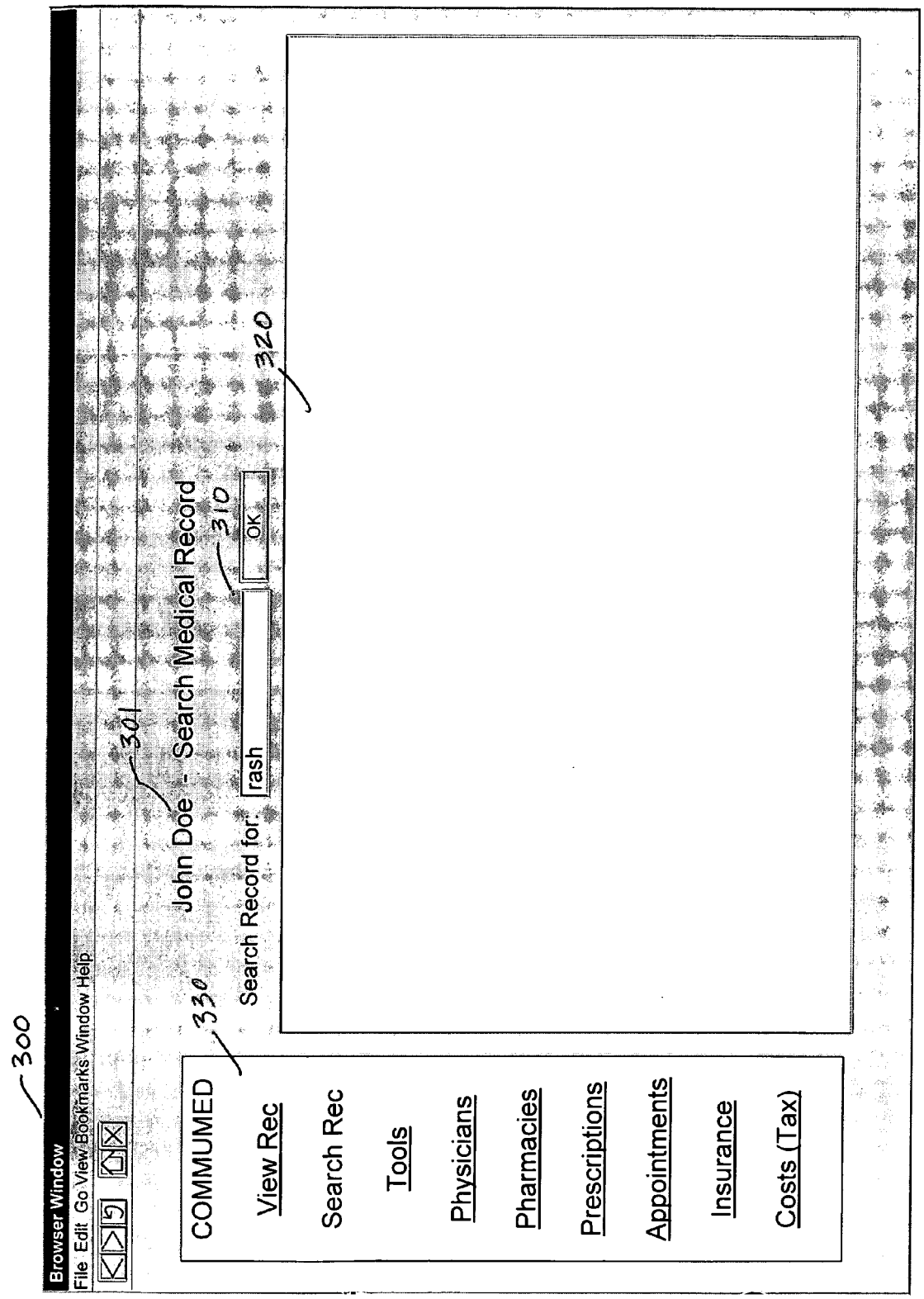
FIG. 3 discloses a second example of a display screen for patient access to their medical record in accordance with the present invention.

FIG. 3 discloses a second example of a display screen from a browser 300 for patient access to their medical record from the "Search Rec" menu choice. In this example, a patient 301 can access records from various medical events or procedures by searching for text or keywords. The desired text or keyword is entered into a search box 310 and results can be displayed in viewing box 320. The results can be listed as hypertext links and navigation back to the list of results can be accomplished using a standard back button of the browser. Access to other viewing tools is provided by menu 330.

Figure 4:
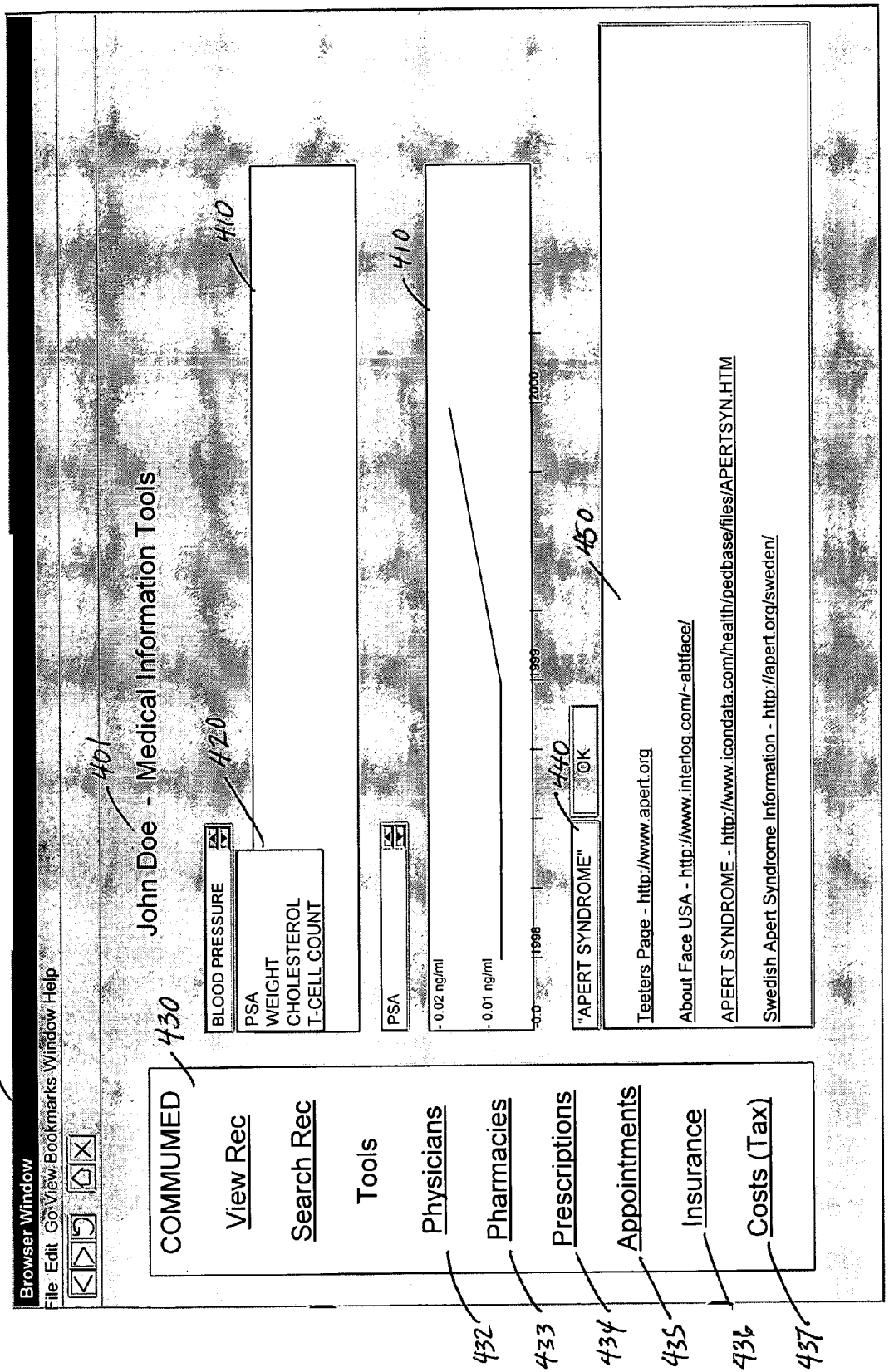
FIG. 4 discloses a third example of a display screen for patient access to their medical record which includes viewing tools in accordance with the present invention.

FIG. 4 discloses a third example of a display screen from a browser 400 for patient access to their medical record that includes viewing tools from the "Tools" menu choice. In this example, a patient 401 can access graphs 410 of specific medical indicia, such as blood pressure, PSA, weight, cholesterol level, t-cell count, etc., over time chosen from pull down menu 420. Although only one graph 410 would typically be needed, two have been shown for clarity. In addition to the previously described viewing tool menu 430, the window can also include a network or Internet search box 440 and viewing box 450. Again, the results can be listed as hypertext links and navigation back to the list of results can be accomplished using a standard back button of the browser.

Additional viewing tools from menu 430 can include other such pages. A "Physicians" page 432 could list the names, addresses, phone numbers, e-mail, and Web page URLs for each of a patient's physicians. This page could also include selectable links for driving directions/maps, web-to-phone calling, e-mailing, physician home pages, Web-based appointment scheduling, etc.

A "Pharmacies" page 433 could list the names, addresses, phone numbers, e-mail, and Web page URLs for each of a patient's pharmacies. This page could also include selectable links for driving directions/maps, web-to-phone calling, e-mailing, pharmacy home pages, Web-based prescription refilling, etc.

A "Prescriptions" page 434 could list the medication, dosage, prescribing physician, and prescription number for each of a patient's prescriptions. This page could also include selectable links for applicable drug information, driving directions/maps to pharmacies, web-to-phone pharmacy calling, e-mail refilling, pharmacy home pages, Web-based prescription refilling, etc.

An "Appointments" page 435 could list the dates, times, names, addresses, phone numbers, e-mail, and Web page URLs for each of a patient's scheduled appointments. This page could also include selectable links for driving directions/maps, web-to-phone calling, e-mailing, appointment web pages, Web-based appointment scheduling, recommended dates for future appointments, etc.

An "Insurance" page 436 could list the names, addresses, phone numbers, e-mail, and Web page URLs for each of a patient's medical insurers. This page could also include selectable links for driving directions/maps, web-to-phone calling, e-mailing, medical insurer home pages, Web-based claim submission and tracking, etc.

A "Costs (Tax)" page 437 could list the payee (name, address), date, amount, form of payment, procedure paid for, amount covered by insurance, etc. for each item of a patient's medical costs. This page could also include selectable links for searching external tax information, exporting data for tax purposes (i.e. TurboTax (™) from Intuit (™), exporting data for financial purposes (i.e. Quicken (™) from Intuit (™)), printing "receipts", etc.

Figure 5:
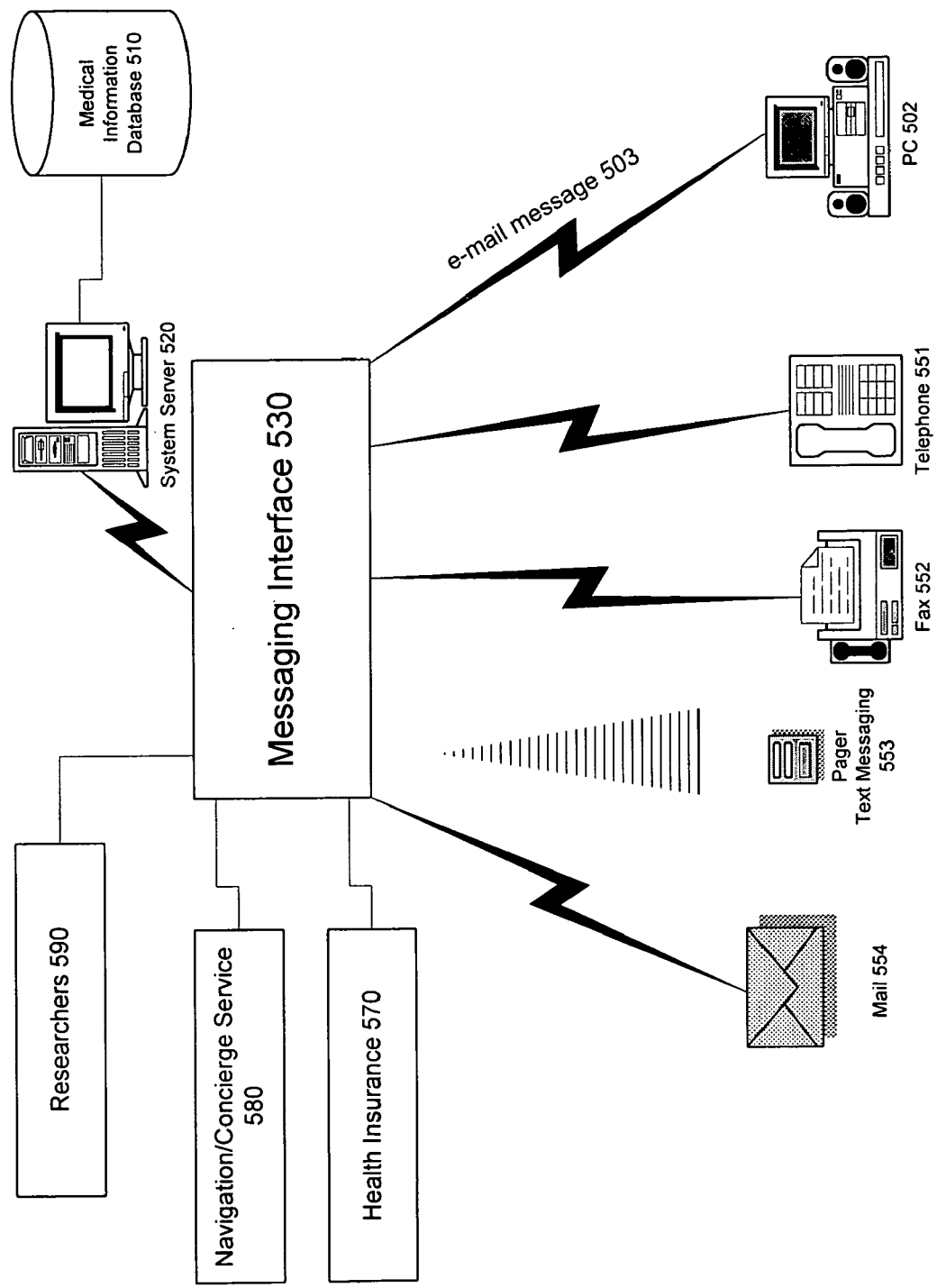
FIG. 5 discloses some of the options with respect to parties and communication mediums for interfacing with the system of the present invention.

FIG. 5 discloses some of the options with respect to parties and communication mediums for interfacing with the system of the present invention.

The system can be setup to schedule and keep track of medical appointments, and can even use server 520 and a suitable messaging interface 530 to notify the patient by e-mail 503 to their PC 502, by recorded message to telephone 551, by facsimile transmission to fax 552, by wireless text messaging to pager or text-messaging phone 553, or by postcard in mail 554 of impending appointments or adjustments to appointments, such as cancellations. It can also be used to verify that appointments have been kept, by offering, for example, email notification to the family/caretaker of Alzheimer patients. Important messages from the system server 520 regarding information, such as medication recalls or results of diagnostic tests, can also be delivered over these channels. Patients can select which of these services they prefer.

Messaging interface 530 can also use these channels for other types of services. For example, insurance claim forms can be automatically generated by server 520 and sent to the patient's health insurance 570 via computer communication, fax 552 or mail 554. The system can also be tied in with third parties, including navigation/concierge services 580, such as ONSTAR (™) and MOBILE Phone (™), so a patient-subscriber can, when it traveling, be directed to the nearest hospital, doctor, or pharmacy by the shortest route and have their pertinent medical information forwarded by server 520 to the location. The navigation/concierge services 580 could contact a part of messaging interface 530 with the patient's request, and server 520 could send the information to the appropriate medical provider's computer or have the messaging interface 530 forward it by fax 552.

The system can also be used, with the patients permission, by medical researchers 590. As an example, pharmaceutical companies could verify reliability and effectiveness of the dosages of medications. The system server 520 could search or flag appropriate patients, send e-mail or browser-form questionnaires to patient PC's 502 and forward results to researchers 590. The system allows the advantages of a large patient database and the information gathering can be accomplished without revealing the patient's name, but rather by using such statistics as age, sex, health status, other medications taken, previous illness, etc. Part of the business plan for the system can include compensation by researchers for access to this valuable database.

A portion of the messaging interface 530 can also interact with mail 554 and fax 552 to input ordinary paper records into the data base 510. This function, preferably using electronic scanning and optical character recognition (OCR) technology, is useful for various situations. Its primary use is for initially transferring a patients records from a hard copy format to an electronic format when initiating use of the service. It can also be used for maintaining/updating the patient's electronic medical record with patient-acquired hard copy records after the patient has visited a non-networked, uncooperative, or otherwise non-participating medical provider. Any suitable form of data capture, even manual input, can be used for the transfer.

Also, in regard to maintaining a complete and accurate record, messaging interface 530 could be used to import patient medical records from other systems. One use for this would be the transfer of electronic medical records from the military before their destruction upon a patient's discharge from the military. Another use for this would be the collection of a patient's medical information from publically-available and commercial sources in order to perform an audit. If any incorrect records are discovered, appropriate action can be taken to correct the errors. If any records are found which legally violate the patient's privacy, appropriate action can be taken to have those records expunged.

In operation, the present invention can provide numerous benefits.

When the system of FIG. 1 is deployed on the Internet, the patient's medical record can be accessed from any browser connected to the Internet after authorization is given via a patient supplied identifier. As a first benefit, this allows the patient's medical record to be quickly accessed when the patient is traveling.

Patients can also get second opinions without the embarrassment of asking the first physician to forward their medical record to the second physician. In this scenario, the patient supplied identifier the can be used by the second physician to allow access the patient's medical record on the database without the involvement of the first physician.

Additionally, dangerous medication interactions and mistakes can be avoided through use of the present invention. Medication interactions and correctness can be checked by the server 120 at multiple points in order to catch mistakes. When a physician prescribes a medication at an office or hospital 140 and uploads the information, the server 120 can be programmed to immediately check for possible interactions and flag problems, thereby allowing the physician the opportunity to prescribe an alternative medication. Additionally, since the server can access data related to the patient's weight, age, sex, allergies, etc., possibly inappropriate medications or dosages can also be flagged.

When pharmacies 140 fill the prescriptions, the server can again be programmed to check for possible interactions or dosage problems. The provision of this function on the server also allows the patient to have drug interactions checked without having to have all of their prescriptions filled by the same pharmacy, as required by existing drug interaction systems.

Additionally, mistakes due to misinterpreting physician handwriting can be avoided by having the prescription downloaded from database 100 electronically and mistakes due to misfilling can be avoided by requiring the pharmacist to scan the bar code of the prescribed medication to match it with the downloaded data before delivery to the patient.

When nurses or physicians dispense or deliver medical treatment to the patient in a hospital 140, the system can assure: (i) proper patient identification by requiring input of a patient supplied identifier, such as a bar coded patient bracelet, prior to administering medication to the patient; (ii) proper medication by requiring input of the medication identification, such as from the bar code on the packaging, prior to administering medication to the patient; and (iii) proper dosage by requiring input of this information prior to administering medication to the patient. For delivery devices, the setting, for example, of correct dosage rates can be made a prerequisite for computer operation of the device.

To prevent mistakes, all of this input information is checked for correctness by software on the server or by an online or offline hospital system using electronic patient record information obtained from the server upon patient authorization. When a medical provider, such as a hospital, is authorized to obtain a patient's electronic medical record for offline use, a prerequisite for such authorization and use can be that the record that is updated offline by the hospital be regularly updated or synced online with the server. An additional prerequisite can be that the electronic patient medical record information obtained from the server be removed or expunged from the medical providers offline usage system when treatment is completed.

The system can also be used by hospitals and pharmacies for inventory control and automatic reordering since medications/dosages are input into the patient medical record when dispensed. As part of the business plan, the system could be programmed to track medical provider inventories, generate inventory reports, and/or automatically reorder supplies for a fee.

The system can also be used to contact physicians and patients immediately after diagnostic labs have posted test results in a patient's electronic medical record.

Although providing medical provider access to electronic medical records on the data base and ability to add/modify records on the data base is an important aspect of the present invention, numerous software packages and systems for providing these functions have already been developed in the prior art (see, for example, "The Creation of a Virtual Electronic Medical Record", Kazmer et al., employed at the University of Virginia Medical Center) and the necessary programming and data base design for the present invention is well within the ability of the ordinary practitioner.

While the description above refers to particular embodiments of the present invention, it will be understood that many modifications may be made without departing from the spirit thereof. The accompanying claims are intended to cover such modifications as would fall within the true scope and spirit of the present invention. The disclosed embodiments are therefore to be considered as illustrative and not as restrictive. The scope of the invention is defined by the appended claims.

I claim:

1. A patient-controlled electronic medical record system comprising:
   a medical information server connected to a network;
   a medical information database connected to the medical information server;
   a plurality of patient medical records stored on the medical information database;
   a plurality of medical provider computers connected to the network and having software to communicate with the medical information server;
   means for patients to allow medical provider computers to access patient-selected portions of the patient's medical record for viewing and adding to the patient's medical record; and
   means for patients to access all portions of their medical record using browser software on a computer connected to the network.

2. The patient-controlled electronic medical record system of claim 1, wherein the medical information server includes software means for formatting patient-selected medical data from their medical record for viewing by patients.

3. The patient-controlled electronic medical record system of claim 1, wherein the medical information server includes software means for generating medical reminders to patients.

4. The patient-controlled electronic medical record system of claim 3, wherein the medical reminders are transmitted by a medium selected from the group consisting of electronic mail, facsimile transmission, telephone, telephonic text messaging, pager, and mail.

5. The patient-controlled electronic medical record system of claim 1, wherein the medical provider computer software is a browser client.

6. The patient-controlled electronic medical record system of claim 1, wherein the network is a public network.

7. The patient-controlled electronic medical record system of claim 6, wherein the public network is the Internet.

8. The patient-controlled electronic medical record system of claim 1, wherein the means for patients to allow medical provider computers to access patient-selected portions of the patient's medical record for viewing and adding to the patient's medical record is a patient-supplied unique access identification means.

9. The patient-controlled electronic medical record system of claim 8, wherein the patient-supplied unique access identification means is selected from the group consisting of alpha-numeric passphrases, smart cards, biometric samples, bar coded cards, and bar coded bracelets.

10. The patient-controlled electronic medical record system of claim 1, wherein the server includes software to check patients' written and filled prescriptions for interactions, allergies, age-dosage suitability, weight-dosage suitability, and sex-appropriateness.

11. The patient-controlled electronic medical record system of claim 1, wherein the server includes software to track medical provider inventories.

12. The patient-controlled electronic medical record system of claim 11, wherein the server further includes software to produce inventory reports for medical providers.

13. The patient-controlled electronic medical record system of claim 11, wherein the server further includes software to automatically reorder depleted inventory items for medical providers.

14. The patient-controlled electronic medical record system of claim 1, wherein the server includes software to schedule patient appointments.

15. The patient-controlled electronic medical record system of claim 14, wherein the server further includes software and interface means to notify patients with reminders or adjustments of scheduled appointments by means selected from the group consisting of telephone voice messaging, facsimile, wireless text messaging, e-mail, and mail.

16. The patient-controlled electronic medical record system of claim 1, wherein the server includes software to track patient medical costs.

17. The patient-controlled electronic medical record system of claim 1, wherein the server includes software to anonymously identify appropriate patients or anonymously extract appropriate data for medical research requests.

18. The patient-controlled electronic medical record system of claim 1, wherein the server includes software to respond to patient-preauthorized requests from third parties to electronically transmit medical record information to a remote location.

19. A method for patient control of an electronic medical record comprising:
  connecting a medical information server to a network;
  connecting a medical information database to the medical information server;
  storing a plurality of patient medical records on the medical information database;
  connecting a plurality of medical provider computers to the network wherein said medical provider computers include software to communicate with the medical information server;
  providing patients with means to allow medical provider computers to access patient-selected portions of the patient's medical record for viewing and adding to the patient's medical record; and
  providing patients means for accessing all portions of their medical record using browser software on a computer connected to the network.

20. The method for patient control of an electronic medical record of claim 19, wherein medical information server software formats patient-selected medical data from their medical record for viewing by patients.

21. The method for patient control of an electronic medical record of claim 19, wherein the medical information server software generates medical reminders to patients.

22. The method for patient control of an electronic medical record of claim 21, wherein the medical reminders are transmitted by a medium selected from the group consisting of electronic mail, facsimile transmission, telephone, telephonic text messaging, pager, and mail.

23. The method for patient control of an electronic medical record of claim 19, wherein the medical provider computers use a browser client to interact with the medical information server.

24. The method for patient control of an electronic medical record of claim 19, wherein the network used is a public network.

25. The method for patient control of an electronic medical record of claim 24, wherein the public network used is the Internet.

26. The method for patient control of an electronic medical record of claim 19, wherein providing patients with means to allow medical provider computers to access patient-selected portions of the patient's medical record for viewing and adding to the patient's medical record uses a patient-supplied unique access identification means.

27. The method for patient control of an electronic medical record of claim 26, wherein the patient-supplied unique access identification means used is selected from the group consisting of alpha-numeric passphrases, smart cards, biometric samples, bar coded cards, and bar coded bracelets.

28. The method for patient control of an electronic medical record of claim 19, wherein the server software checks patients' written and filled prescriptions for interactions, allergies, age-dosage suitability, weight-dosage suitability, and sex-appropriateness.

29. The method for patient control of an electronic medical record of claim 19, wherein the server software to tracks medical provider inventories.

30. The method for patient control of an electronic medical record of claim 29, wherein the server software produces inventory reports for medical providers.

31. The method for patient control of an electronic medical record of claim 29, wherein the server software automatically reorders depleted inventory items for medical providers.

32. The method for patient control of an electronic medical record of claim 19, wherein the server software operates to schedule patient appointments.

33. The method for patient control of an electronic medical record of claim 32, wherein the server software further operates with interface means to notify patients with reminders or adjustments of scheduled appointments by means selected from the group consisting of telephone voice messaging, facsimile, wireless text messaging, e-mail, and mail.

34. The method for patient control of an electronic medical record of claim 19, wherein the server software tracks patient medical costs.

35. The method for patient control of an electronic medical record of claim 19, wherein the server software to anonymously identifies appropriate patients or anonymously extracts appropriate data for medical research requests.

36. The method for patient control of an electronic medical record of claim 19, wherein the server software responds to patient-preauthorized requests from third parties to electronically transmit medical record information to a remote location.

37. The patient-controlled electronic medical record system of claim 1, further comprising means for transferring hard copy medical record information into an electronic format for storage in the medical information database.

38. The method for patient control of an electronic medical record of claim 19, further comprising transferring hard copy medical record information into an electronic format for storage in the medical information database.

39. The patient-controlled electronic medical record system of claim 1, further comprising means for collecting and transferring patient medical record information from other sources in an electronic format for storage in the medical information database.

40. The method for patient control of an electronic medical record of claim 19, further comprising collecting and transferring patient medical record information from other sources in an electronic format for storage in the medical information database.

41. The patient-controlled electronic medical record system of claim 39, further comprising means for auditing the patient medical record information from other sources and correcting the patient medical record information from other sources as needed.

42. The method for patient control of an electronic medical record of claim 40, further comprising auditing the patient medical record information from other sources and correcting the patient medical record information from other sources as needed.

43. The patient-controlled electronic medical record system of claim 1, further comprising means for transferring a complete patient medical record from the medical information database to a medical provider for temporary offline use.

44. The method for patient control of an electronic medical record of claim 19, further comprising transferring a complete patient medical record from the medical information database to a medical provider for temporary offline use.

45. The patient-controlled electronic medical record system of claim 1, wherein medical provider software is an e-mail client and means for sending patient medical record information associated with the server responds to an order selected from the group consisting of preauthorized events, patient requests, and medical provider requests sent to an autoresponder using patient supplied information.

46. The method for patient control of an electronic medical record of claim 19, wherein medical provider software is an e-mail client and patient medical record information is sent in response to an order selected from the group consisting of preauthorized events, patient requests, and medical provider requests to an autoresponder using patient supplied information.

* * * * *